United States Patent
Ashraf

(10) Patent No.: US 7,501,034 B2
(45) Date of Patent: Mar. 10, 2009

(54) METHOD FOR PRODUCING A CORRUGATED STRETCH LAMINATE

(75) Inventor: Arman Ashraf, Hamilton, OH (US)

(73) Assignee: The Procter & Gamble Company, Cincinnati, OH (US)

(*) Notice: Subject to any disclaimer, the term of this patent is extended or adjusted under 35 U.S.C. 154(b) by 469 days.

(21) Appl. No.: 10/966,759

(22) Filed: Oct. 15, 2004

(65) Prior Publication Data

US 2006/0083900 A1    Apr. 20, 2006

(51) Int. Cl.
B32B 37/00 (2006.01)

(52) U.S. Cl. .................. 156/200; 156/210; 156/229; 156/307.3

(58) Field of Classification Search ............. None
See application file for complete search history.

(56) References Cited

U.S. PATENT DOCUMENTS

| | | | |
|---|---|---|---|
| 1,974,209 A | 9/1934 | Fowler | |
| 2,957,200 A | 10/1960 | Herman et al. | |
| 3,085,292 A | 4/1963 | Kindseth | |
| 3,848,594 A | 11/1974 | Buell | |
| 3,860,003 A | 1/1975 | Buell | |
| 4,329,309 A | 5/1982 | Kelly | |
| 4,606,964 A | 8/1986 | Wideman | |
| 4,626,305 A | 12/1986 | Suzuki et al. | |
| 4,662,875 A | 5/1987 | Hirotsu et al. | |
| 4,846,815 A | 7/1989 | Scripps | |
| 4,847,134 A * | 7/1989 | Fahrenkrug et al. | 428/138 |
| 4,894,060 A | 1/1990 | Nestegard | |
| 4,946,527 A | 8/1990 | Battrell | |
| 5,151,092 A | 9/1992 | Buell et al. | |
| 5,221,274 A | 6/1993 | Buell et al. | |
| 5,422,172 A * | 6/1995 | Wu | 442/62 |
| 5,554,145 A | 9/1996 | Roe et al. | |
| 5,569,234 A | 10/1996 | Buell et al. | |
| 5,580,411 A | 12/1996 | Nease et al. | |
| 6,004,306 A | 12/1999 | Robles et al. | |
| 6,432,098 B1 | 8/2002 | Kline et al. | |
| 2003/0088228 A1 | 5/2003 | Desai et al. | |
| 2003/0091807 A1 | 5/2003 | Desai et al. | |
| 2004/0005835 A1 | 1/2004 | Zhou et al. | |
| 2004/0049836 A1 | 3/2004 | Ashraf et al. | |
| 2004/0123938 A1 | 7/2004 | Neculescu et al. | |
| 2004/0162538 A1 | 8/2004 | Mueller et al. | |
| 2004/0222553 A1 | 11/2004 | Desai et al. | |
| 2006/0083893 A1 | 4/2006 | Ashraf | |

* cited by examiner

FOREIGN PATENT DOCUMENTS

| | | |
|---|---|---|
| EP | 0 672 516 A | 9/1995 |
| WO | WO 01/87588 | 11/2001 |
| WO | WO 01/88245 | 11/2001 |
| WO | WO 03/039420 A | 5/2003 |
| WO | WO 03/039421 A | 5/2003 |
| WO | WO 2004/098475 | 11/2004 |

OTHER PUBLICATIONS

PCT Search Report, mailed Oct. 2, 2006, 4 pages.

*Primary Examiner*—Richard Crispino
*Assistant Examiner*—Barbara J. Musser
(74) *Attorney, Agent, or Firm*—Charles R. Matson; Eric T. Addington

(57) ABSTRACT

A process for making a corrugated stretch laminate comprising the steps of providing a first carrier web having a first surface and a second surface; applying a first elastomeric composition in a fluid or molten state to the first surface of the carrier web to form at least one first elastic member; incrementally stretching in a first direction at least a portion of the carrier web to form a stretch composite preform; elongating the stretch composite preform in the first direction; joining a first substrate to the elongated stretch composite preform; and allowing the elongated stretch composite preform to recover to form said corrugated stretch laminate.

16 Claims, 8 Drawing Sheets

METHOD FOR PRODUCING A CORRUGATED STRETCH LAMINATE

FIELD OF THE INVENTION

This invention relates to a method of forming a corrugated stretch laminate via applying a fluid or molten elastomeric composition onto a carrier web and joining the carrier web to a substrate.

BACKGROUND

Disposable absorbent products like diapers typically include stretchable materials in the waist region and the cuff regions to provide a snug fit and a good seal of the article. Pant-type absorbent articles further include stretchable materials in the side portions for easy application and removal of the article and for sustained fit of the article. Stretchable materials have also been used in the ear portions for adjustable fit of the article. The stretchable materials utilized in these article regions may include elastomeric materials such as films, nonwovens, strands, scrims, and the like. In most cases, these designs deliver uniform and unidirectional stretch, most often in the lateral direction of the article. However, elastomeric materials are relatively expensive so their use in stretchable materials may be desirably optimized. Additionally, if elastomeric materials are used without some type of cover material, the elastomeric materials may tend to exhibit increased drag on skin surface, which may result in discomfort to the wearer of the product.

Stretchable materials may be made in the form of a stretch laminate, which involves one or more elastomeric materials laminated to one or more layers of another material. While the laminate may improve wearer comfort, the laminate may exhibit more limited stretchability and/or considerable resistance to stretch. It would be desirable to address this resistance to stretch in order to make more desirable stretch laminates.

One approach for creating stretch laminates is by a stretch bonding method. Stretch bonded laminates are made by stretching an elastic in a first direction, bonding the stretched elastic to one or more materials such as a nonwoven, and releasing the tension from the elastic so that the materials gather. The elastic may be supplied to the process (e.g., elastic strands purchased from a supplier) or formed in-situ within the process. The resulting laminate typically will be extensible in the same direction in which the elastic was stretched. The gathered nonwoven tends to have a corrugated feel and increased caliper that can improve wearer comfort when such stretch bonded laminates are used in absorbent products. The gathered nonwoven may also exhibit improved opacity; a feature that may be desirable since improved opacity often suggests a high quality product. However, stretch bonding has its problems. Handling stretched elastic strands presents processing difficulties that may reduce the speed of the manufacturing line. Furthermore, achieving secure attachment of elastic strands to the nonwoven may be difficult to achieve and/or to maintain. The cost of elastic strands and the means of attachment (e.g., an adhesive) can become prohibitively high. Furthermore, elastic strands may not be able to impart the requisite elasticity to the stretch laminate, such as multi-directional stretch or variable stretch in a given vector.

Some stretch laminates may be formed from an elastic film instead of discrete elastic strands. While such an approach may impart multi-directional stretch and requisite elasticity, elastic films are usually far more costly than strands. Furthermore, elastic films are generally not breathable, which may result in discomfort to the wearer of the product. While elastic films may be perforated to improve breathability, such perforation comes as an additional step and with additional cost. A further disadvantage of elastic films is that it is difficult and costly to provided variability in the elastic forces of a given film.

An alternate approach that is capable of delivering a multidirectional, non-uniform stretch laminate is disclosed in copending U.S. application Ser. Nos. 10/288,095, 10/288,126, and 10/429,433. This approach involves hot melt application of one or more thermoplastic elastomers onto a substrate (e.g., nonwoven), followed by incremental stretching of the substrate that confers the stretch properties of the elastomer to the substrate in a somewhat magnified form. Suitable application methods disclosed therein include direct gravure, offset gravure, and flexographic printing. Each of these methods allow deposition of any amount of an elastomer in any shape and direction, thus giving a wide variety of design flexibility which ultimately results in improved fit of the overall diaper product. However, the hot melt application method can be improved. Incremental stretching can physically break the fiber to fiber network within a nonwoven. As a result, an incrementally stretched nonwoven may appear shredded and be aesthetically undesirable. The shredded appearance can be avoided by using a nonwoven with a sufficiently high basis weight, but with increased basis weight comes increased cost. Furthermore, it is difficult for the hot melt application method to yield a stretch laminate that exhibits a gathered appearance as found in stretch-bonded laminates. Without a gathered nonwoven, the benefits of corrugated feel and increased caliper are missing. Furthermore, the opacity of stretch laminates resulting from the hot melt method can exhibit reduced opacity as compared to a similarly constructed stretch bonded laminate (i.e., the stretch bonded laminate and hot melt laminate having nonwovens of like construction and basis weight).

In view of the above, it would be desirable to provide a cost effective stretch laminate having elastomeric materials disposed only in specific areas in specific amounts to provide a desired in-use benefit (e.g., sealing, containing, gasketing, body-conforming) for an article. It would also be desirable to provide an efficient and cost-effective process for producing the stretch laminates. Further, it would be desirable to provide a process for producing stretch laminates that exhibit gathering or corrugation such that feel and caliper are improved. It would also be desirable to provide a process for producing stretch laminates that exhibit a high degree of opacity.

SUMMARY OF THE INVENTION

The present invention relates to a process for making a corrugated stretch laminate comprising the steps of providing a first carrier web having a first surface and a second surface; applying a first elastomeric composition in a fluid or molten state to the first surface of the carrier web to form at least one first elastic member; incrementally stretching in a first direction at least a portion of the carrier web to form a stretch composite preform; elongating the stretch composite preform in the first direction; joining a first substrate to the elongated stretch composite preform; and allowing the elongated stretch composite preform to recover to form the corrugated stretch laminate.

In certain embodiments of the present invention, the step of applying the first elastomeric composition is performed by applying the first elastomeric composition with a device such as a bath, a slot coater, a sprayer, an extruder, a print rolls/web, a gravure roll/web, a reverse roll, a knife-over roll, a notch knife-over roll, a metering rod, a curtain coater, an air knife coater, and combinations thereof.

In certain embodiments, the process may further comprise the step of applying a second elastomeric composition in a fluid or molten state to the carrier web to form at least one second elastic member.

In certain embodiments, the process for making a corrugated stretch laminate may comprise the steps of providing a first carrier web having a first surface and a second surface; stretching in a first direction at least a portion of the carrier web; applying a first elastomeric composition in a fluid or molten state to the first surface of the carrier web to form at least one first elastic member and to form a stretch composite preform; elongating the stretch composite preform in a second direction; joining a first substrate to the elongated stretch composite preform; and allowing the elongated stretch composite to recovery to form said corrugated stretch laminate.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings.

DETAILED DESCRIPTION

Figure 1:
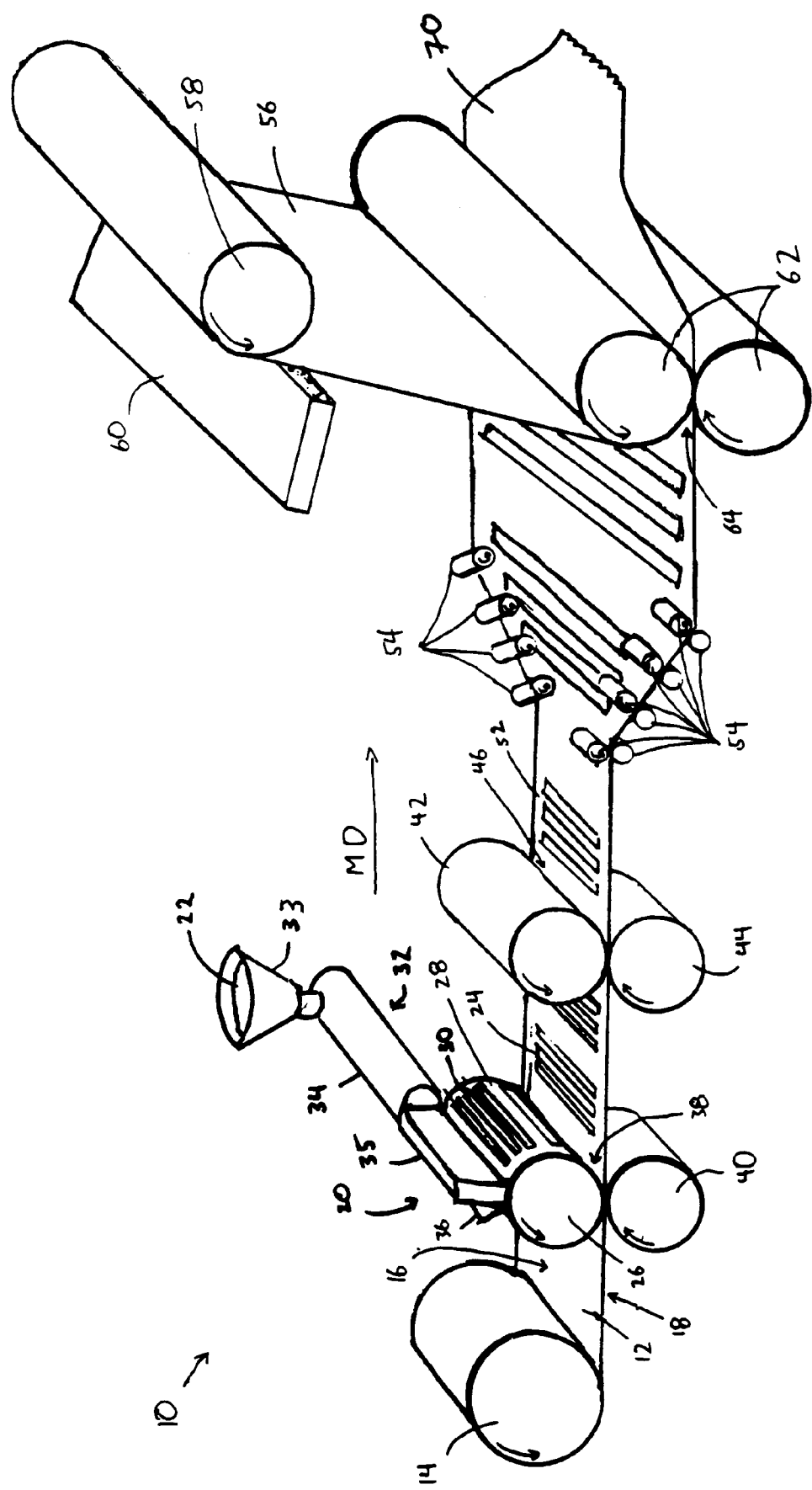
FIG. 1 is a schematic illustration of a representative process of the present invention.

The term "disposable" as used herein refers to products which generally are not intended to be laundered or otherwise restored or extensively reused in their original function, i.e., products that are intended to be discarded after a single use or a small number of uses. It is preferred that such disposable articles be recycled, composted or otherwise disposed of in an environmentally compatible manner.

The term "disposable absorbent article" as used herein refers to a device that normally absorbs and retains fluids. In certain instances, the phrase refers to devices that are placed against or in proximity to the body of the wearer to absorb and contain the excreta and/or exudates discharged from the body, and includes such personal care articles as fastened diapers, pull-on diapers, refatenable/prefastened diapers and pants, training pants, swim diapers, adult incontinence articles, feminine hygiene articles, and the like. In other instances, the term also refers to protective or hygiene articles, for example, bibs, wipes, bandages, wraps, wound dressings, surgical drapes, and the like.

The term "fibrous substrate" as used herein refers to a material comprised of a multiplicity of fibers that could be either a natural or synthetic material or any combination thereof, for example, nonwoven webs, woven webs, knitted fabrics, and any combinations thereof.

The term "substrate" as used herein refers to a material that includes either a natural or synthetic material or any combination thereof, for example, nonwoven webs, woven webs, knitted fabrics, films, film laminates, nonwoven laminates, sponges, foams, and any combinations thereof.

The term "nonwoven" as used herein refers to a material made from continuous and/or discontinuous fibers, without weaving or knitting, by processes including, but not limited to, spun-bonding, carding and melt-blowing. The nonwoven webs can comprise one or more nonwoven layers, wherein each layer can include continuous and/or discontinuous fibers. Nonwoven webs can also comprise bicomponent fibers, which can have core/shell, side-by-side, or other known fiber structures.

The term "elastic" or "elastomeric" as used herein refers to any material that upon application of a biasing force, can stretch to an elongated length of at least about 160 percent of its relaxed, original length, without rupture or breakage, and upon release of the applied force, recovers at least about 55% of its elongation. The material desirably may recover substantially to its original length. That is, the recovered length may be less than about 120 percent, may be less than about 110 percent, or may be less than about 105 percent of the relaxed original length.

The term "inelastic" refers herein to any material that does not fall within the definition of "elastic" above.

The term "elastomer" as used herein refers to a polymer exhibiting elastic properties.

The term "extensible" or "inelastically elongatable" refers herein to any material that upon application of a biasing force to stretch beyond about 110 percent of its relaxed original length will exhibit permanent deformation, including elongation, rupture, breakage, and other defects in its structure, and/or changes in its tensile properties.

The term "necked material" refers to any material that has been narrowed in one direction by the application of a tensioning force.

The term "machine direction" (alternatively referred to herein as "MD") is a well known term of art that is generally understood to refer to the direction corresponding to the length of a web as it is formed or processed. The machine direction typically corresponds to the path the web travels during formation or processing.

The term "cross-machine direction" (alternatively referred to herein as "CD") refers to the direction which is 90° to the machine direction.

One process of the present invention, which will be described in more detail herein, relates to a process of manufacturing a corrugated stretch laminate including the steps of providing a carrier web; applying a first elastomeric composition in a fluid or molten state either directly or indirectly to the carrier web to form at least one first elastic member; incrementally stretching in a first direction at least a portion of the carrier web to form a stretch composite preform; elongating the stretch composite preform in the first direction; and joining at least one first substrate to the elongated stretch composite preform to form said corrugated stretch laminate upon recovery of the elongated stretch composite preform. The resultant corrugated stretch laminate exhibits elasticity in at least the first direction.

Illustrated in FIG. 1 is one embodiment of a process 10 of manufacturing a corrugated stretch laminate 70. In this embodiment, the process 10 may include the steps of: providing a carrier web; applying a first elastomeric composition in a fluid or molten state either directly or indirectly to the carrier to form at least one first elastic member; incrementally stretching in a cross-machine direction at least a portion of the carrier web to form a stretch composite preform; elongating the stretch composite preform in the cross-machine direction; and joining at least one first substrate to the elongated stretch composite preform. Upon recovery of the elongated stretch composite preform/first substrate laminate, a corrugated stretch laminate is formed exhibiting stretch and recovery in at least the cross-machine direction.

Providing a Carrier Web

A carrier web 12 may be provided in a substantially continuous manner (i.e., web is supplied continuously during the normal operation of the process) such as from a bulk supply roll 14. The carrier web 12 may have a first surface 16 and second surface 18. Suitable carrier webs 12 may include films, knitted fabric, woven fibrous webs, nonwoven fibrous webs, laminates, or combinations thereof. In certain embodiments, the carrier web 12 may include a fibrous substrate such as an extensible nonwoven web that comprises polyolefin fibers and/or filaments. The carrier web 12 may also be a laminate comprising a fibrous substrate such as a nonwoven-film laminate, which for example, may be used as the outer-cover of a disposable diaper, training pant, adult incontinence product, etc. In certain embodiments, the carrier web 12 may have a basis weight of about 3 g/m$^2$ to about 45 g/m$^2$. In other embodiments, the carrier web 12 may have a basis weight of about 5 g/m$^2$ to about 25 g/m$^2$. However, carrier web 12 can be of lesser or greater basis weight depending upon the intended application of the resultant corrugated stretch laminate.

The carrier web 12 may be removed from the bulk supply roll 14 by rotating the bulk supply roll 14. The rotation of the bulk supply roll 14 may be powered by a variable speed motor capable of ramping up or down based on operational demand. The carrier web 12 is fed to an application device 20. In other embodiments, the carrier web 12 may be provided by on-line formation. In such an embodiment, the process 10 may be equipped with a formation station where the carrier web 12 is created. Methods for creating a carrier web 12 such as, for example, films, knitted fabric, woven fibrous webs, nonwoven fibrous webs, laminates, or combinations thereof are well known in the art. For example, the carrier web 12 may comprise a nonwoven web comprising spunbonded filaments; a spunbond extrusion station may be utilized to provide the carrier web 12.

Applying a First Elastomeric Composition

Application of a first elastomeric composition 22 to the first surface 16 of the carrier web 12 to form an elastic member 24 may be performed according to a variety of direct and indirect application methods and by a variety of application devices 20 including baths, slot coaters, sprayers, extruders, print rolls/webs, reverse rolls, knife over rolls, metering rods, curtain coaters, air knife coaters, porous rolls, and combinations thereof. In FIG. 1, the application device 20 is shown to be a gravure print device. Gravure printing involves either a gravure printing roll 26 or gravure printing belt. When a roll 26 is employed, as shown in FIG. 1, the gravure roll 26 has an exterior surface 28 interspersed with one or more cells (or grooves) 30. The gravure roll 26 may exhibit rotation about an axis that runs parallel to the cross-machine direction. When a belt is employed, the printing belt has an exterior surface comprising one or more grooves. The cells or grooves 30 are indentations on the exterior surface 28 of the roll 26 (or belt) that permit receipt of a fluid or flowable material (e.g., the elastomeric composition 22) that is intended for transfer from the roll to another surface (e.g., the carrier web 12). Since temperature can affect the viscosity and, consequently, the processing character of the elastomeric composition 22, it may be desirable that the roll 26 or belt is capable of being heated and/or cooled relatively quickly so that the process can run at a commercially-reasonable speed. Furthermore, as the elastomeric composition 22 is being transferred from the gravure roll 26 to the carrier web 12, the elastomeric composition 22 may be in a fluid phase or have sufficient flowability so as to at least partially penetrate the carrier web 12. The relative dimensions of the cells 30 may be varied to impart specific stretch characteristics or geometries to the resultant corrugated stretch laminate.

A fluid or molten elastomeric composition 22 may be delivered to the gravure roll 26 by a delivery mechanism 32. The delivery mechanism 32 can be any device that supplies an amount of elastomeric composition 22 to the gravure roll 26. Suitable delivery mechanisms 32 include, for example, devices such as slot coaters, baths, sprayers, or extruders. As illustrated in FIG. 1, the delivery mechanism 32 involves an extruder 34 delivering the elastomeric composition 22 to the rotating gravure roll 26. The extruder 34 is provided in proximity to the exterior surface 28 of the gravure roll 26. The extruder 34 may receive the elastomeric composition 22 from a feeder 33. The extruder 34 may heat, mix, consolidate, transport, and/or process the elastomeric composition 22. The extruder may extrude the elastomeric composition 22 through an apertured die 35. The extruder 34 and/or die 35 may meter the extrusion such that a defined amount of elastomeric composition 22 is delivered to the gravure roll 26 per unit time. The elastomeric composition 22 flows onto the exterior surface 28 of the gravure roll 26 and into the cells 30. A doctor blade 36 may be provided to wipe the exterior surface 28 of the gravure roll 26 substantially free of any residual elastomeric composition 22. The doctor blade 36 is also useful in providing for uniform distribution of the elastomeric composition 22 into the cells 30.

The elastomeric composition 22 may be applied in a fluid, fluid-like, or molten state to affect at least partial penetration into the carrier web 12. Partial penetration results in mechanical locking of the elastomeric composition 22 and the carrier web 12 such that the resulting elastic member 24 will not exhibit excessive delamination during subsequent processing or manufacturing steps or in the finished product. The degree of penetration may be affected by several factors including the viscosity of the elastomeric composition 22 when in contact with the carrier web 12, the porosity of the carrier web 12, the surface tension between the carrier web 12 and the elastomeric composition 22, and/or subsequent processing steps. The gravure roll 26 may be temperature controlled so that the elastomeric composition 22 is at an ideal viscosity so as to improve penetration of the elastomeric composition 22 into the carrier web 12. Further discussion of the interaction between a molten, fluid, and/or fluid-like elastomeric composition 12 and a relatively cooler roll is discussed in U.S. application Ser. No. 60/557,272 filed on Mar. 29, 2004.

The carrier web 12 may be brought into contact with the rotating gravure roll 26 at a nip point 38. The cells 30 filled with the elastomeric composition 22 are brought into contact with the carrier web 12. The elastomeric composition 22 may be partially or fully emptied from the cell 30 and onto the first surface 16 of the carrier web 12. The gravure roll 26 may be paired with a back-up roll 40. The back-up roll 40 rotates on an axis parallel to the axis of rotation for the gravure roll 26. The back-up roll 40 may be made from or coated with a relatively pliant material such as silicone rubber having a hardness of about 55 Shore A. It may be desirable that the back-up roll 34 is capable of being heated and/or cooled. The gravure roll 26 and back-up roll 40 meet at the nip point 38. The temperature and pressure applied at the nip point 38 by the gravure roll 26 and back-up roll 40 may further control the degree penetration of elastomeric composition 22 into the fibrous carrier web 12. Increased nip pressure may result in increased penetration of the elastomeric composition 22 into the fibrous network of the carrier web 12. In some cases, it may be desirable to enhance penetration only in some areas of contact between the carrier web 12 and the elastomeric composition 22. For example, this can be accomplished with the use of a patterned, instead of smooth, back-up roll 40 during printing. For example, the back-up roll 40 can have longitudinal (MD) cells or grooves whereby less pressure is exerted at the nip point when the backup roll cells are proximate to the nip point. Furthermore, the contact time of a discrete a point of a carrier web 12 within the nip point 38 can be adjusted to give optimum bonding Other suitable embodiments may include more than one application device 20. A carrier web 12 may be subjected to two or more applications of an elastomeric composition 22. For example, the carrier web 12 may be subjected to a first application device applying a first elastomeric composition and a second application device applying a second elastomeric composition. The first and second application devices may include baths, slot coaters, sprayers, extruders, print rolls/webs, reverse rolls, knife over rolls, metering rods, curtain coaters, and air knife coaters. The first and second application devices may be the same or different. Likewise, the first and second elastomeric compositions may be the same composition or may be different. The first and second elastomeric compositions result in first elastic members and second elastic members. The first and second elastic members may be discrete or interconnected (i.e., overlapping, adjoining). In some embodiments, the first and second elastic members differ in a property such as elasticity, melt viscosity, shape, pattern, add-on level, and combinations thereof.

It is possible to vary the amount of elastomeric composition 22 deposited in different portions of the carrier web 12, thereby varying the local stretch properties. For example, by altering the depth and/or width of cells 30 on the roll 26, the resulting elastomeric members 24 can be thicker in one area and thinner in another area. In another example, by changing the pattern on the gravure printing roll 26, the resulting elastomeric members 24 can exhibit varying member densities (i.e., numbers of elastomeric members 24 per unit area) from one area to another area of the composite.

The stretch property of the printed carrier web 12 can be varied discretely (i.e., the property changes in a stepwise manner) by varying the deposition the elastomeric composition 22. An example of such stepwise change would be to apply a first elastomeric composition in one portion of the carrier web 12 and a second elastomeric composition in another portion of the carrier web 12. The stretch property can also be varied continuously, either linearly or non-linearly. The continuous changes in stretch property may be achieved by the cell 30 pattern design. For example, the cell 30 depth may decrease gradually along the length of the cell 30, thus resulting in a printed pattern where the amount of deposited elastomeric composition 22 decreases continuously from one end of the elastic member 24 to the other.

The relative dimensions of resulting elastic member 24 may be varied to impart specific stretch characteristics or geometries to the resultant corrugated stretch laminate. As shown in FIG. 1, the elastic members 24 may substantially or intermittently span the cross-machine direction width of the carrier web 12. Clearly one skilled in the art may alter the relative size, shape, and orientation of the elastic members 24 by altering the gravure cell 30 size, shape, and orientation or by altering the formulation, delivery, and deposition of the elastomeric composition 22.

Alternatively, an indirect transfer application device, such as off-gravure printing, may be used to apply the elastomeric composition 22. Indirect application involves depositing the elastomeric composition 22 to an intermediate surface which then may deposit the elastomeric composition 22 onto the carrier web 12. For example, the gravure roll cells 30 may apply the elastomeric composition 22 to an intermediate surface (e.g., a transfer roll or a carrier substrate) having good thermal stability, which is then brought into contact with the carrier web 12 thereby transferring the elastomeric composition 22. The indirect transfer method may allow for a wider range of operating temperatures because the fluid or molten elastomeric composition 22 is partially cooled when it contacts the carrier web 12. Thus, the indirect process may be useful for carrier webs 12 that are thermally sensitive or unstable, such as nonwoven webs, or substrates of low melting polymers, including polyethylene and polypropylene.

Stretching the Carrier Web

The printed carrier web 12 (i.e., the carrier web 12 with the elastomeric composition 22 deposited thereon to form elastic members 24) may be subjected to stretching. In some embodiments of the present invention, incremental stretching may be desired. Incrementally stretching the printed carrier web 12 elongates the generally elongatable but inelastic carrier web 12 and converts the printed carrier web 12 into a stretch composite preform 52. As a result of this structural change, the carrier web 12 exhibits reduced resistance to stretch and the elastomeric members 24 may be able to stretch to the extent provided by the permanent elongation of the carrier web 12.

In one embodiment, an incremental stretch process commonly referred to as "ring-rolling," may be a desirable method by which to stretch the printed carrier web 12. In the ring-rolling process, corrugated interengaging forming rolls 42, 44 are used to permanently elongate the printed carrier web 12 to reduce its resistance to stretch. The resulting stretch composite preform 52 has a greater degree of stretchability in the portions that have been subjected to the ring-rolling process, and, thus, providing additional flexibility in achieving stretch properties in localized portions of the stretch composite.

As shown in FIG. 1, ring-rolling is incorporated into process 10. The printed carrier web 12 is fed into the nip 46 formed by a pair of opposed forming rolls 42, 44. The opposing forming rolls 42, 44 incrementally stretch and elongate the printed carrier web 12, thereby converting the printed carrier web 12 into stretch composite preform 52.

Figure 2:
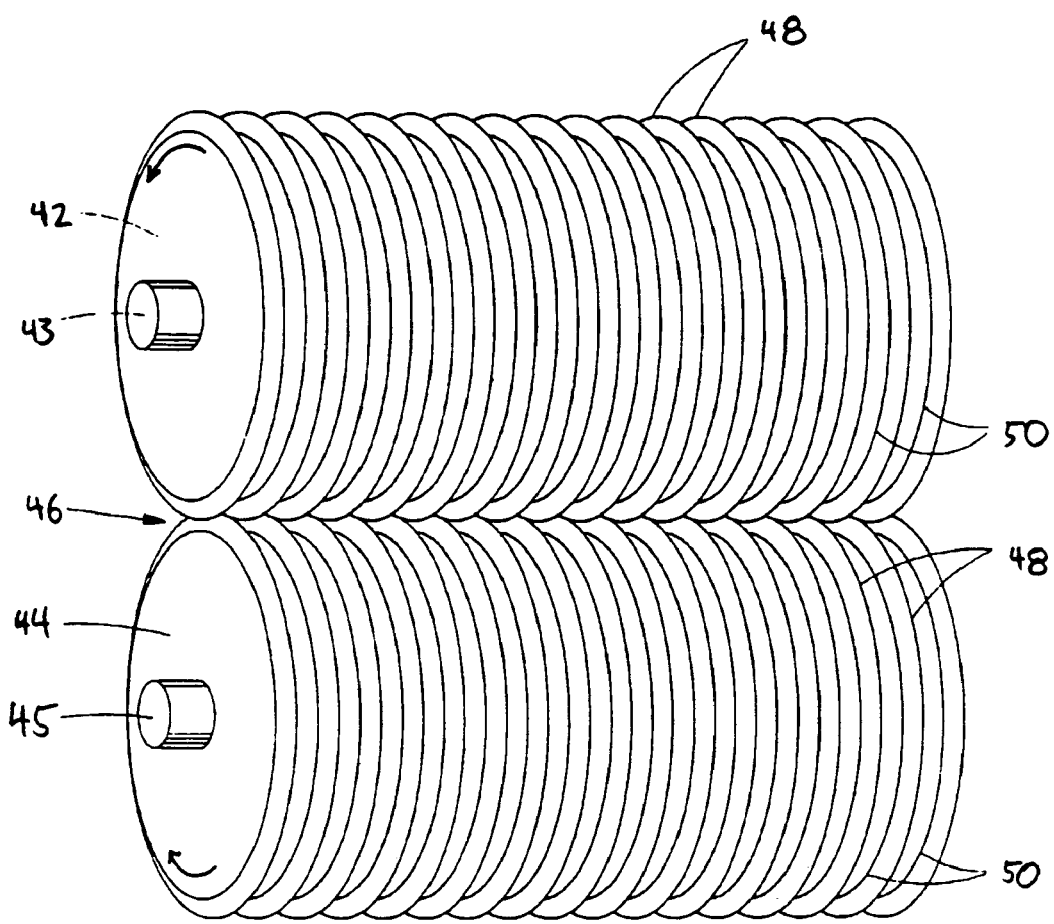
FIG. 2 is an enlarged perspective view of the interengaging forming rolls, as presented in FIG. 1, which are used to incrementally stretch a carrier web.

Exemplary structures and relative positions of forming rolls 42, 44 are shown in an enlarged perspective view in FIG. 2. As shown, rolls 42, 44 may be carried on respective rotatable shafts 43, 45 having their axes of rotation disposed in parallel relationship. While the shafts 43, 45 of the rolls 42, 44 are shown as being substantially oriented in the cross-machine direction, the axes may be canted with regard to the cross-machine direction. Each of rolls 42, 44 may include a plurality of axially-spaced, side-by-side, circumferentially-extending, equally-configured teeth 48, respectively, that can be in the form of thin fins of substantially rectangular cross section, or they can have a triangular or an inverted V-shape when viewed in cross section. The outermost tips of the teeth 48 may be rounded to avoid cuts or tears in the materials that pass between the rolls.

The spaces between adjacent teeth 48 define recessed, circumferentially-extending, equally configured grooves 50. The grooves 50 can be of substantially rectangular cross section when the teeth 48 are of substantially rectangular cross section, and they can be of inverted triangular cross section when the teeth 48 may be of triangular cross section. Thus, each of forming rolls 42, 44 includes a plurality of spaced teeth 48 and alternating grooves 50 between each pair of adjacent teeth 48. The teeth 48 and the grooves 50 need not each be of the same width. For example, the grooves 50 may have a larger width than that of the teeth 48 to permit the carrier web that passes between the interengaged rolls 42, 44 to be received within the respective grooves 50 and to be locally stretched. Furthermore, the distance between grooves 50 and/or the distance between teeth 48 may be of variable widths. While the rolls 42, 44 are shown having interengaging teeth 248 and grooves 250 that run substantially in the machine direction (±45° from the machine direction), the teeth 48 and grooves 50 may also run in the cross-machine direction (i.e., ±45° from the cross machine direction) or in a curvilinear pattern.

Figure 3:
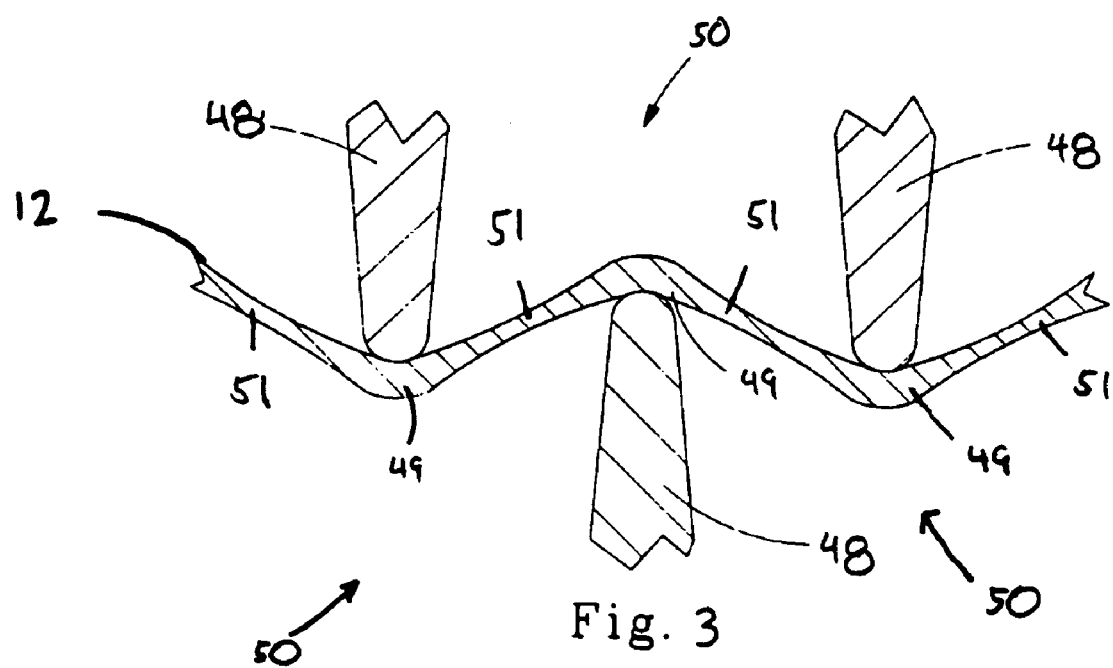
FIG. 3 is an enlarged fragmentary cross-sectional view of the interengaging forming rolls, as presented in FIG. 2, with the carrier web between interengaged teeth and grooves.

FIG. 3 is an enlarged cross-sectional view of interengaged teeth and grooves with the printed carrier web 12 being modified therebetween. As shown, a portion of the printed carrier web 12 is received between the interengaged teeth 48 and grooves 50 of the respective rolls 42, 44. The interengagement of the teeth 48 and grooves 50 of the rolls 42, 44 causes laterally spaced portions of the printed carrier web 12 to be pressed by teeth 48 into opposed grooves 50. In the course of passing between the forming rolls 42, 44, the forces of teeth 48 pressing the printed carrier web 12 into opposed grooves 50 impose within printed carrier web 12 tensile stresses that act in the cross-web direction. The tensile stresses cause intermediate portions 51 of the carrier web 12 that lie between and span the spaces between the tip portions of adjacent teeth 48 to stretch or extend in a cross-web direction, which results in a localized reduction of the web thickness as well as web tensile strength at each of intermediate portions 48.

The action of pressing portions of the printed carrier web 12 into the respective grooves 50 by teeth 48 generally causes a non-uniform reduction of the thickness of the printed carrier to take place in the cross-web direction of the composite. The portions of the carrier web 12 that are in contact with the tooth tips typically reduce only slightly in thickness. Conversely, the intermediate portions 51 of the carrier web 12 span adjacent teeth 48 generally exhibit more substantial thinning. Thus, by passing through the forming rolls 42, 44 and being locally laterally stretched by spaced grooves 50 and teeth 48, the carrier web 12 develops alternating high and low basis weight regions.

Further discussion regarding methods for imparting stretchability to an extensible or otherwise substantially inelastic material by using corrugated interengaging rolls which incrementally stretch in the machine and/or cross-machine direction and permanently deform the material is provided in U.S. Pat. Nos. 4,116,892; 4,834,741; 5,143,679; 5,156,793; 5,167,897; 5,422,172; and 5,518,801. In some embodiments, the carrier web 12 may be subjected to two or more ring-rollings that may impart stretchability in more than one direction (e.g, ring-rolling in the machine and cross-machine directions to impart machine and cross-machine direction stretch). Alternatively, incremental stretching of the printed carrier web 12 may be performed by a pair of interengaging grooved planar plates or other means for incremental stretching (i.e., not rolls) the carrier web 12.

The amount of incremental stretch provided by the forming rolls 42, 44 can be varied as needed for the intended use of the resultant corrugated stretch laminate 70 (e.g., use in an absorbent article). In some embodiments, when the resultant corrugated laminate 70 is used in a waist band of an absorbent article, the carrier web may be stretched in excess of about 50%. In some embodiments, for example when the resultant corrugated stretch laminate is used in a side panel of a pant-type absorbent article, the carrier web may be stretched in excess of about 200%. Incremental stretching of the carrier web in excess of 200% or less than 50% may also be achieved.

While the teeth 48 and grooves 50 of the forming rolls 42, 44 are shown as being equally spaced and substantially parallel to one another, such a configuration is not to be read as limiting. The teeth 48 and grooves 50 may follow a curvilinear path on the forming rolls 42, 44 so as to provide varying degrees and/or vectors of elasticity along the resultant corrugated stretch laminate. Furthermore, the forming rolls 42, 44 may have varying frequency of teeth 48 and grooves 50 and varying depths of engagement between the teeth 48 and grooves 50. Such variation may result in corrugated stretch laminate that exhibits variable stretch in that some areas are easily elastically elongatable and other areas may resist elongation.

Elongating the Stretch Composite Preform

Referring to FIG. 1, the stretch composite preform 52 may be subjected to tensioning, which results in elongation of the stretch composite preform 52 and the elastic members 24 therein or thereon. The elongation of the stretch composite preform 52 may be performed in the same direction as the incremental stretching is performed (i.e., a printed carrier web 12 incrementally stretched in a cross machine direction is desirably elongated in a cross machine direction). The preform 52 may be elongated up to the point of catastrophic failure; however, the preform 52 is ideally elongated to a point less than or about equal to the percent elongation achieved during the prior stretching step. Methods for tensioning and elongating process webs are well known in the art. Elongation in the cross machine direction can be accomplished by subjecting the stretch composite to "Mount Hope" rolls, tentering frames, angled idlers, angled nips, slatted spread rollers, edge pull web stretchers, and the like, each of which is known to those skilled in the art. As shown in FIG. 1, cross machine direction elongation may be achieved through the use of one or more edge pull rollers 54. The edge pull rollers 54 form a nip point through which the stretch composite preform 52 may be fed. The edge pull rollers 54 may be canted outwardly from the machine direction path of travel of the preform 52. The canting creates a cross-machine direction vector of force that strains and elongates the preform 52. The angle of canting off from the machine direction may be varied to impart cross-machine direction force vectors of varying magnitude. Such varied canting may be used to gradually increase the cross-machine direction vector of force that may be applied the preform 52, which is believed to reduce catastrophic failure of the preform 52. A series of edge pull rollers 54 are shown in FIG. 1. The use of a series of edge pull rollers 54 may be used to achieve the requisite elongation of the stretch composite preform 52. Furthermore, a series of edge pull rollers 54 may allow for a graduated elongation of the preform 52 so as to prevent imposition of violent web strain and potential failure of the preform 52.

The stretch composite preform 52 is elongated an effective amount such that the resultant corrugated stretch laminate 70 exhibits at least some degree of corrugation. In certain embodiments, the stretch composite preform 52 is elongated from at least about 50% to about 150%. In other embodiments, the stretch composite preform 52 is elongated at least about 150% to about 250%. Elongation in excess of 250% or less than 50% may also be performed.

Joining a Substrate

The elongated stretch composite preform 52 is joined to a first substrate 56. The first substrate 56 may be provided in a substantially continuous manner (i.e., web is supplied continuously during the normal operation of the process) such as from a bulk supply roll 58. The first substrate 56 may have a first surface and second surface. Suitable first substrates 56 may include films, knitted fabric, woven fibrous webs, non-woven fibrous webs, laminates, or combinations thereof. In certain embodiments, the first substrate 56 is a fibrous substrate such as an extensible nonwoven web that comprises polyolefin fibers and/or filaments. The first substrate 56 may also be a laminate comprising a fibrous substrate such as a nonwoven-film laminate, which for example, may be used as the outercover of a disposable diaper, training pant, adult incontinence product, etc. The first substrate 56 may be removed from the bulk supply roll 58 by rotating the bulk supply roll 58. The rotation of the bulk supply roll 58 may be powered by a variable speed motor capable of ramping up or down based on operational demand. In other embodiments, the first substrate 56 may be provided by on-line formation. In such an embodiment, the process 10 may be equipped with a formation station where the first substrate 56 is created. Methods for creating a first substrate 56 such as, for example, films, knitted fabric, woven fibrous webs, nonwoven fibrous webs, laminates, or combinations thereof are well known in the art. For example, the first substrate 56 may comprise a nonwoven web comprising spunbonded filaments; a spunbond extrusion station may be utilized to provide the first substrate 56.

The first substrate 56 and the elongated stretch composite preform 52 may be bonded to one another in a face-to-face relationship, such that one substantially planar surface of the preform 52 may be bonded to one substantially planar surface of the first substrate 56. The planar face of the elongated stretch composite preform 52 with the elastic members 24 applied thereon may be the face bonded to the first substrate 56. Bonding of the first substrate 56 and the elongated stretch composite preform 52 may be conducted by a variety of bonding methods well known in the art such as adhesive, thermal, mechanical, ultrasonic bonding. Bonding may be relatively continuous or intermittent. Relatively continuous bonding implies that the first substrate 56 and the stretch composite preform 52 are bonded together over substantially all of one or more dimensions of a common interface between the first substrate 56 and the stretch composite preform 52. Intermittent bonding implies that the first substrate 56 and the stretch composite preform 52 are bonded together with one or more individual, discrete bonds that are not continuous or bond patterns having open areas free of bonds. As illustrated in FIG. 1, bonding may be performed by use of a first adhesive applicator 60 positioned between the bulk supply roll 58 and bonding rolls 62. The first adhesive applicator 60 applies an effective amount of adhesive to join the first substrate 56 and the stretch composite preform 52. An effective amount of adhesive may be applied so as to prevent delamination during normal use conditions of the resultant corrugated stretch laminate 70. Adhesive may be applied to the first substrate 56, the stretch composite preform 52, or to both. In other embodiments, the elastic members 24 on or within the elongated stretch composite preform 52 may exhibit residual adhesive character such that use of an adhesive may be unnecessary.

The adhesive-bearing first substrate 56 and the elongated stretch composite 52 may be brought together in a face-to-face relationship by way of the bonding rolls 62. The bonding rolls 62 may form a bonding nip 64 whereby the first substrate and composite are brought into contact and may be compressed. Compression may improve adhesive spread and/or penetration into the preform 52 and the substrate 56 thus providing for a stronger adhesive bond. In the case of thermo-mechanical bonding, the bonding rolls 62 may impart bonding by heat and/or pressure so as to fuse the substrate 56 and preform 52.

The printed carrier web 12 and/or the stretch composite preform 52 may be subjected to additional treatments such as cooling, pressing (e.g., passing between a pair of nip rolls), crosslinking, curing (e.g., via chemical, thermal, radiation methods), heating, ring-rolling, and combinations thereof, to enhance the elastic and mechanical properties of the elastomeric composition 22 deposited thereon and/or of the resulting elastic member 24. Upon release of tension, a corrugated stretch laminate 70 results from the bonding of the stretch composite preform 52 to the first substrate 56. The corrugated stretch laminate 70 resulting from the process 10 shown in FIG. 1 exhibits stretch and recovery in at least the cross machine direction.

Figure 4A:
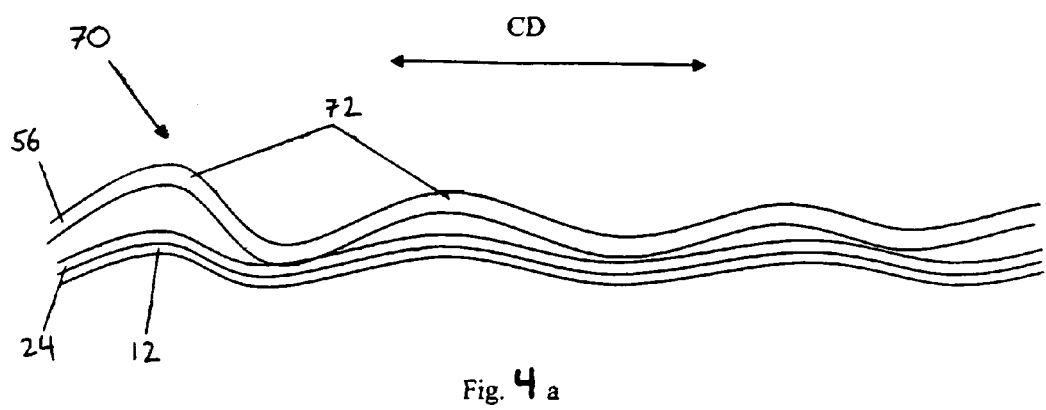
FIG. 4a is an enlarged cross-sectional view of a corrugated stretch laminate in a recovered state wherein tension has been released from the elastic members.
Figure 4B:
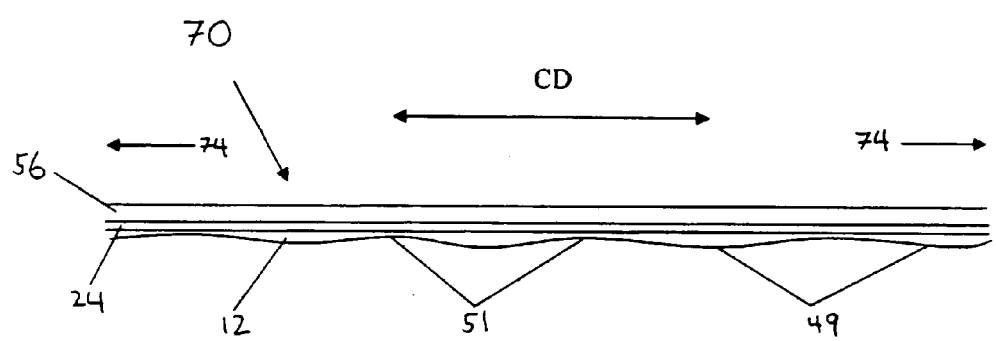
FIG. 4b is an enlarged cross-sectional view of the corrugated stretch laminate of FIG. 4a with a tensioning force applied thereto.

Upon recovery of the elongated stretch composite preform/first substrate laminate, a corrugated stretch laminate 70, as shown in FIGS. 4a and 4b, results. FIG. 4a is an enlarged sectional view along the cross-machine direction of the corrugated stretch laminate 70 in a recovered state wherein tension has been released from the elastic members 24. The first substrate 56 may gather and foreshorten so as to produce a plurality of corrugations 72 in the resultant corrugated stretch laminate 70. Corrugations are the irregular corrugation hills and corrugation valleys that alternate in the corrugated stretch laminate. The carrier web 12 may exhibit corrugation. Corrugation of the carrier web 12 may be an artifact of the incremental stretching. With ring-rolling in particular, the alternating areas of low-basis weight 51 and high-basis weight 49 may exhibit a corrugated look and/or feel. Corrugation of the carrier web 12 may also be an artifact of the corrugation of the first substrate 56.

Once a tensioning force 74 is placed on the corrugated stretch laminate 70, the corrugations 72 may enable the first substrate 56 to extend with the elastic member 24 at least to the point of reaching a force wall, which is about where the corrugations flatten out, as shown in FIG. 4b. As the strain is removed, the elastic member 24 may contract back toward its original, recovered length. This contraction re-establishes the corrugations 72 of the corrugated stretch laminate 70.

Figure 5:
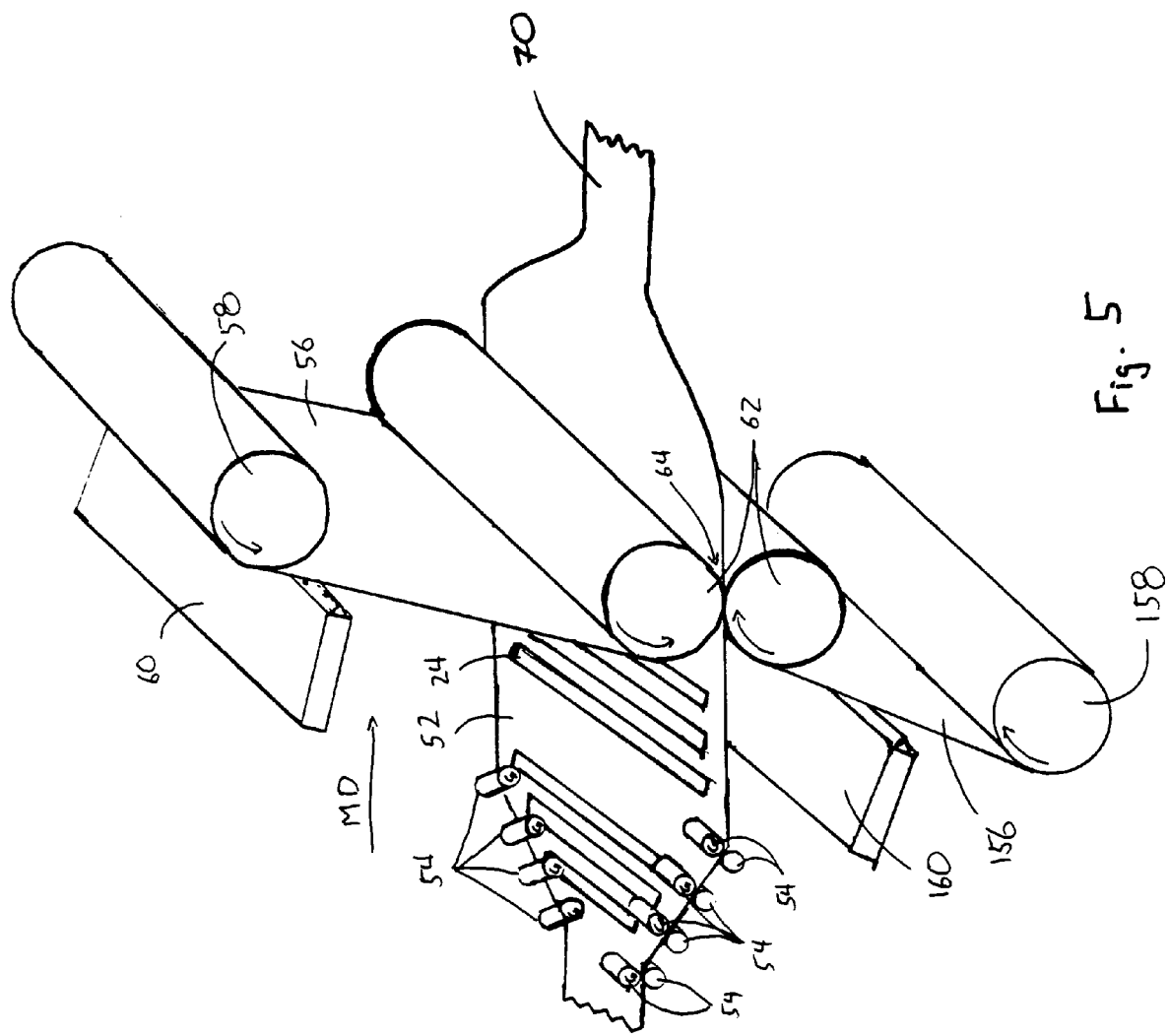
FIG. 5 is a schematic illustration of a representative process of the present invention whereby two substrates are attached to the carrier web.

FIG. 5 illustrates another embodiment of the present process showing the elongation of the stretch composite preform 52 and joining of more than one substrate. All other steps are similar to those presented in FIG. 1. In this embodiment, two substrate are being joined to the elongated stretch composite preform 52. Particularly, a first substrate 56 and a second substrate 156 are being joined to the elongated stretch composite preform 52. As shown in FIG. 5, the first substrate 56 may be joined to the planar face of the elongated stretch composite preform 52 with the elastic members 24 applied thereon or therein. The second substrate 156 may be joined to the opposing planar surface of the elongated stretch composite preform 52. Clearly, the number of substrates to be joined to the elongated stretch composite preform 52 may vary. Likewise, the relative orientation and positioning of the substrates to be joined to the elongated stretch composite preform 52 may vary (e.g., the first and second substrates 56, 156 may be joined to the elongated stretch composite preform in a manner such that the first substrate is between the preform and second substrate).

The second substrate 156 may be provided in a substantially continuous manner (i.e., web is supplied continuously during the normal operation of the process) such as from a bulk supply roll 158. The second substrate 156 may have a first surface and second surface. Suitable second substrates 156 may include films, knitted fabric, woven fibrous webs, nonwoven fibrous webs, laminates, or combinations thereof. The second substrate may be a fibrous substrate such as an extensible nonwoven web that comprises polyolefin fibers and/or filaments. The second substrate 156 may also be a laminate comprising a fibrous substrate such as a nonwoven-film laminate, which for example, may be used as the outer-cover of a disposable diaper, training pant, adult incontinence product, etc.

The second substrate 156 may be removed from the bulk supply roll 158 by rotating the bulk supply roll. The rotation of the bulk supply roll 158 may be powered by a variable speed motor capable of ramping up or down based on operational demand. As with the first substrate 56 described above, the second substrate 156 may also be provided by on-line formation.

Bonding of the first and second substrates 56, 156 and the elongated stretch composite preform 52 may be conducted by a variety of bonding methods well known in the art such as adhesive, thermal, mechanical, ultrasonic bonding. Bonding may be relatively continuous or intermittent. As illustrated in FIG. 5, bonding may be performed by use of a first adhesive applicator 60 positioned between the first bulk supply roll 58 and a bonding roller device 62 and by use of a second adhesive applicator 160 positioned between the second bulk roll 158 and the bonding roller device 62. The adhesive applicators 60, 160 apply an effective amount of adhesive to join the first and second substrates 56, 156 and the stretch composite preform 52. An effective amount of adhesive may be applied so as to prevent delamination during normal use conditions of the resultant corrugated stretch laminate 70. In other embodiments, the elastic members 24 on or within the elongated stretch composite preform 52 may exhibit residual adhesive character such that use of an adhesive may be unnecessary.

The first and second substrates 60, 160 and the elongated stretch composite preform 52 may be brought together in a face-to-face relationship by way of the bonding roller device 62. The bonding rollers 62 may form a bonding nip 64 whereby each substrate 56, 156 may be brought into contact and may be compressed with the preform 52. Compression may improve adhesive spread and/or penetration into the two substrates 56, 156 thus providing for a stronger adhesive bond. In the case of thermo-mechanical bonding, the bonding roller device 62 may impart bonding with heat and/or pressure so as to fuse the two substrates 56, 156 and the preform 52. Upon recovery of the elongated stretch composite preform/first substrate/second substrate laminate, a corrugated stretch laminate 70 results.

Figure 6:
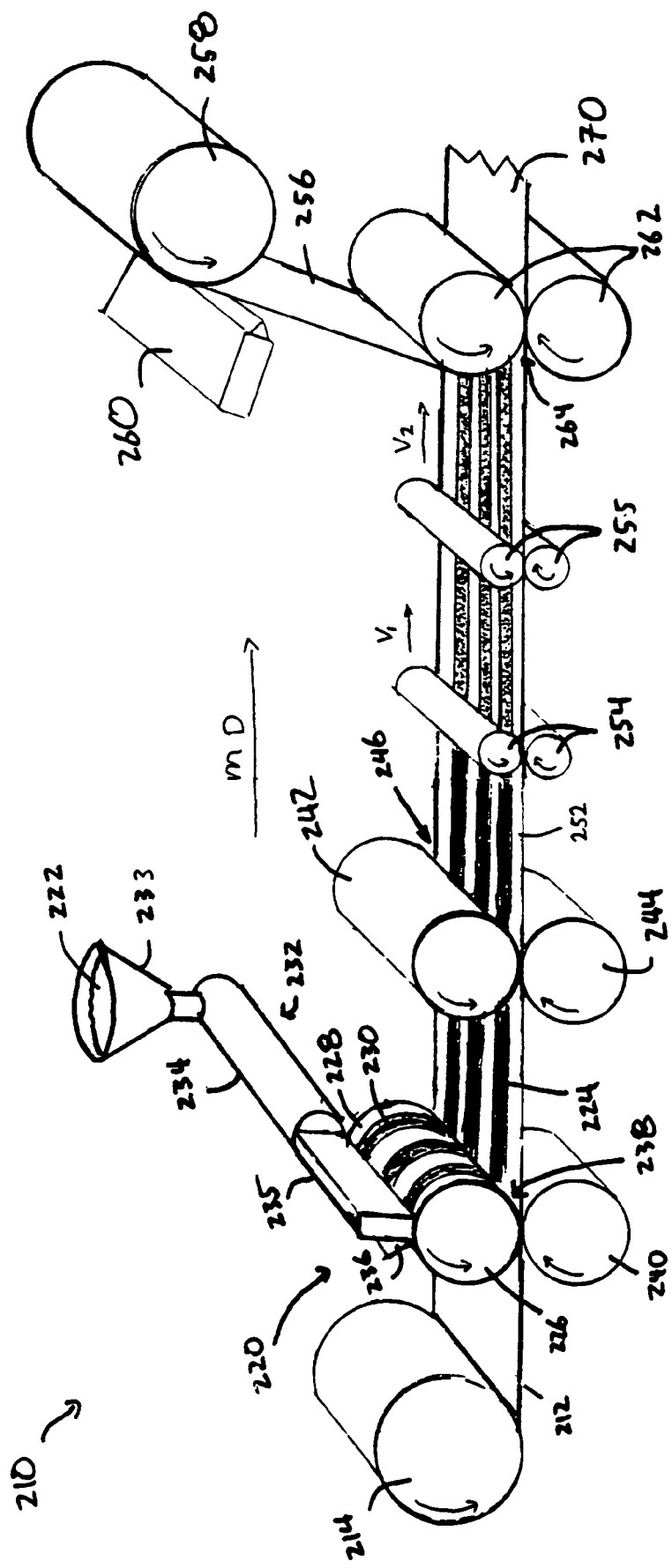
FIG. 6 is a schematic illustration of another representative process of the present invention.

FIG. 6 illustrates another embodiment of the process of the present invention which imparts machine direction stretch to the resultant corrugated stretch laminate 70. A carrier web 212 is supplied by a bulk supply roll 214 and fed to an application device 220. The application device 220 may include a gravure roll 226, a back-up roll 240, a delivery mechanism 232, or others as described herein. The gravure roll 226 has an exterior surface 228 interspersed with one or more grooves 230.

The delivery mechanism 232 involves an extruder 234 delivering the elastomeric composition 222 to the rotating gravure roll 226. The extruder 234 is provided in proximity to the exterior surface 228 of the gravure roll 226. The extruder 234 may receive the elastomeric composition 222 from a feeder 233. The extruder 234 may heat, mix, consolidate, transport, and/or process the elastomeric composition 222. The extruder may extrude the elastomeric composition 222 through an apertured die 235. The extruder 234 and/or die 235 may meter the extrusion such that a defined amount of elastomeric composition 222 is delivered to the gravure roll 226. The elastomeric composition 222 flows onto the exterior surface 228 of the gravure roll 226 and into the cells 230. A doctor blade 236 may be provided to wipe the exterior surface 228 of the gravure roll 226 substantially free of any residual elastomeric composition 222. The doctor blade 236 is also useful in providing for uniform distribution of the elastomeric composition 222 into the cells 230.

The elastomeric composition 222 within the cells 230 of the gravure roll 226 is brought into contact with the carrier web 212 at a nip point 238 to form an elastic member 224. The relative dimensions of resulting elastic member 224 may be varied to impart specific stretch characteristics or geometries to the resultant corrugated stretch laminate. As shown in FIG. 6, the elastic members 224 may substantially or intermittently span the machine direction length of the printed carrier web 212.

The printed carrier web 212 (i.e., the carrier web 212 with the elastomeric composition 222 deposited thereon to form elastic members 224) may be subjected to incremental stretching. The printed carrier web 212 may be incrementally stretched by ring-rolling in the machine direction. Ring-rolling may be conducted by opposing forming rolls 242, 244 having interengaging teeth 248 and grooves 250 that run substantially in the machine direction (±45° from the machine direction), cross machine direction (i.e., ±45° from the cross machine direction), or combinations thereof. The printed carrier web 212 may fed through the opposing forming rolls 242, 244 to yield a stretch composite preform 252.

Figure 7:
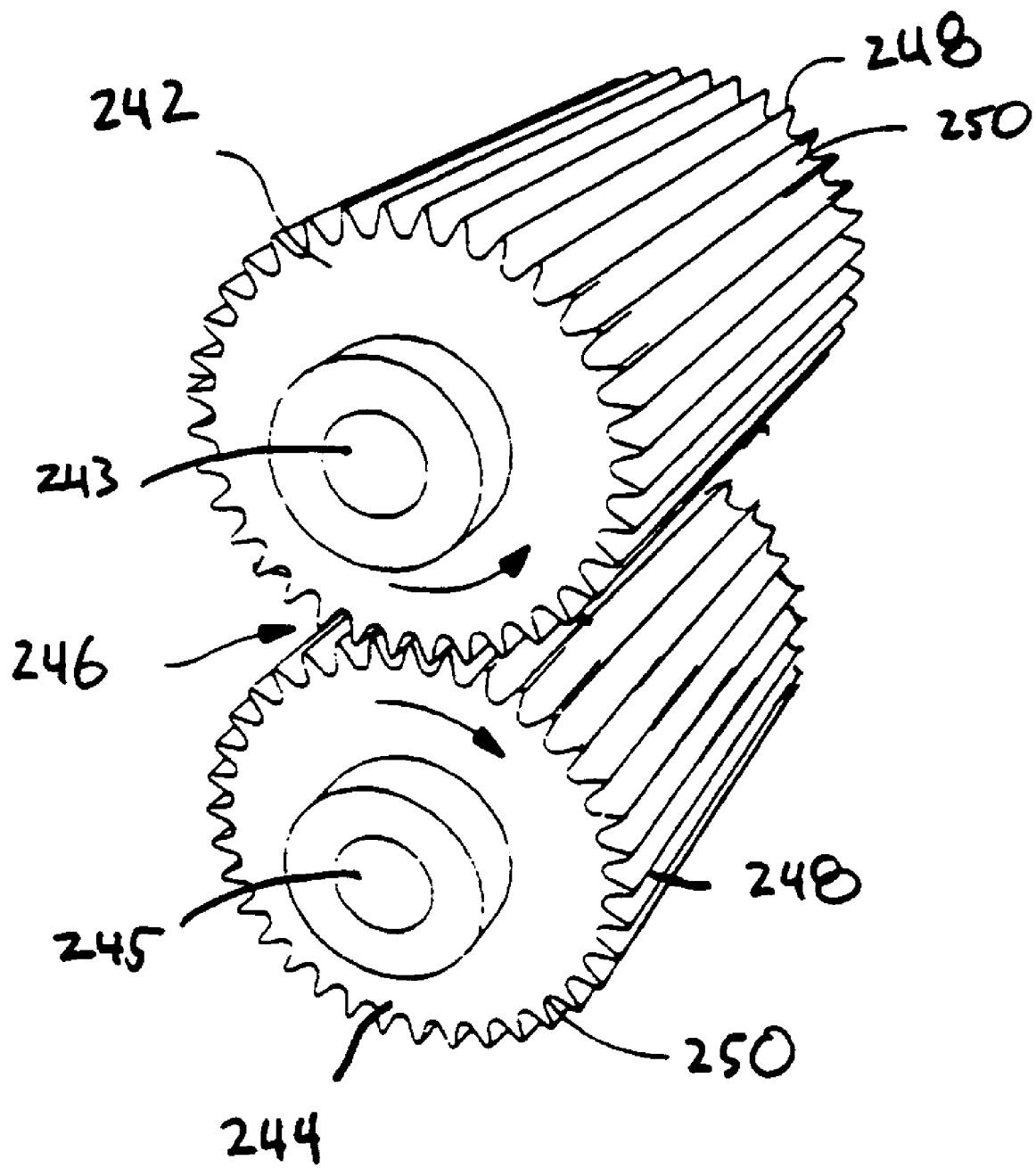
FIG. 7 is an enlarged perspective view of the interengaging forming rolls, as presented in FIG. 6, which are used to incrementally stretch a carrier web.

An exemplary structure of forming rolls 242, 244 is shown in an enlarged perspective view in FIG. 7. As shown, rolls 242, 244 are carried on respective rotatable shafts 243, 245 having their axes of rotation disposed in parallel relationship. While the shafts 243, 245 of the rolls 242, 244 are shown as being substantially oriented in the cross-machine direction, the axes may be canted with regard to the cross-machine direction. Each of rolls 242, 244 includes a plurality of raised, side-by-side, linearly-extending, equally-configured teeth 248 that can be in the form of thin fins of substantially rectangular cross section, or they can have a triangular or an inverted V-shape when viewed in cross section. The outermost tips of the teeth 248 are may be rounded to avoid cuts or tears in the materials that pass between the rolls.

The spaces between adjacent teeth 248 define recessed, linearly-extending, equally configured grooves 250. The grooves 250 can be of substantially rectangular cross section when the teeth 248 are of substantially rectangular cross section, and they can be of inverted triangular cross section when the teeth 48 are of triangular cross section. Thus, each of forming rolls 242, 244 includes a plurality of spaced teeth 48 and alternating grooves 250 between each pair of adjacent teeth 248. The teeth 248 and the grooves 250 need not each be of the same width; however, it is desirable for the grooves 250 to have a larger width than that of the teeth 248 so as to permit the carrier web that passes between the interengaged rolls 242, 244 to be received within the respective grooves 250 and to be locally stretched. Addition description of the ring-rolling process is provided above.

The stretch composite preform 252 may be elongated in the machine direction. Elongation of the stretch composite preform 252 may be performed by means well known in the art. For example, elongation in the machine direction can be accomplished by conveying the stretch composite preform 252 through off-speed rolls. As the name implies, off-speed rolls involve a sequence of rolls driven at increasing speeds. FIG. 6 illustrates a first set of off-speed rolls 254 and a second set of off-speed rolls 255. The first off-speed rolls 254 form a first nip which imparts a first velocity $V_1$ to the stretch composite preform 252 as the preform 252 passes the first nip. The second off-speed rolls 255 form a second nip which imparts a second velocity $V_2$ to the stretch composite preform 252 as the preform 252 passes the second nip. When the second velocity $V_2$ is greater to the first velocity $V_1$, tension may be imparted to stretch composite preform 252 and particularly to the elastic members 224 therein or thereon. The tension may elongate the stretch composite preform 252 in the machine direction. Clearly, to maintain the machine direction elongation, the stretch composite 252 must maintain the second velocity $V_2$ until laminated with a substrate as provided for below. In other suitable embodiments, the number of off-speed rolls 254, 255 may vary and may be omitted altogether. If the off-speed rolls 254, 255 are to be omitted, machine direction elongation may be achieved by imparting the first velocity $V_1$ and second velocity $V_2$ with existing process components. For example, the first velocity $V_1$ may be imparted by the rotational speed of the forming rolls 242, 244 performing the ring-rolling. The second velocity $V_2$ may be imparted by bonding rolls 262 for use in joining a substrate to the stretch composite preform 252 as provided for below. The increase in velocity results in tensioning and elongation of the stretch composite preform 252 between the incremental stretching and the joining of the substrate. In other embodiments, the forming rolls 242, 244; the off-speed rolls 254, 255; and the bonding rolls 262 may impart a varying velocity to the preform 252. A gradually increasing viscosity may be desirable to prevent catastrophic rupture of the preform 252 which may occur with a sudden increase in velocity.

The elongated stretch composite preform 252 may be joined with a first substrate 256. The first substrate 256 may be provided in a substantially continuous manner (i.e., web is supplied continuously during the normal operation of the process) such as from a bulk supply roll 258. In other embodiments, the first substrate 256 may also be provided by on-line formation as described above The first substrate 256 and the elongated stretch composite preform 252 are bonded to one another in a face-to-face relationship, such that one substantially planar surface of the preform 252 may be bonded one substantially planar surface of the first substrate 256. The planar face of the elongated stretch composite preform 252 with the elastic members 224 applied thereon or therein may be the face bonded to the first substrate 256. Bonding of the first substrate 256 and the elongated stretch composite preform 252 may be conducted by a variety of bonding methods well known in the art such as adhesive, thermal, mechanical, ultrasonic bonding. Bonding may be relatively continuous or intermittent. FIG. 6 illustrates an adhesive applicator 260 positioned between the bulk supply roll 258 and a bonding roller device 262. The adhesive applicator 260 applies an effective amount of adhesive to join the first substrate 256 and the stretch composite preform 252. An effective amount of adhesive may be applied so as to prevent delamination of the resultant corrugated stretch laminate 270. The adhesive-bearing first substrate 256 and the elongated stretch composite 252 may be brought together in a face-to-face relationship by way of the bonding roller device 262. The bonding rollers 262 may form a bonding nip 264 whereby the first substrate 256 and composite preform 252 are brought into contact and may be compressed. Compression may improve adhesive spread and/or penetration into the substrates 256 thus providing for a stronger adhesive bond to the preform 252. In the case of thermo-mechanical bonding, the bonding roller device 262 may impart bonding by heat and/or pressure so as to fuse the substrate 256 and composite 252. In other embodiments, the elastic members 224 on or within the elongated stretch composite preform 252 may exhibit residual adhesive character such that use of an adhesive may be unnecessary.

Upon recovery of the elongated stretch composite preform/first substrate laminate, a corrugated stretch laminate 270 results. The corrugated stretch laminate 270 resulting from the process shown in FIG. 6 exhibits stretch and recovery in at least the machine direction. The corrugated stretch laminate 270 may exhibit numerous corrugations in a relaxed state (e.g., no application of a tensioning force). The first substrate 256 may gather and foreshorten so as to produce a plurality of corrugations in the resultant corrugated stretch laminate 270. Corrugations are the irregular corrugation hills and corrugation valleys that alternate in the corrugated stretch laminate. The carrier web 212 may also exhibit corrugation. Corrugation of the carrier web 212 may be an artifact of the incremental stretching. With ring-rolling in particular, the alternating areas of low-basis weight and high-basis weight may tend to exhibit a corrugated look and/or feel. Corrugation of the carrier web 212 may also be an artifact of the corrugation of the first substrate 56 in that the corrugation hills and corrugation valleys in the first substrate 256 may result in correlating corrugation valleys and corrugation hills in the carrier web 212.

Once a tensioning force is placed on the corrugated stretch laminate 270, the corrugations may enable the first substrate 256 to extend with the elastic member 224 at least to the point of reaching a force wall, which is about where the corrugations flatten out. As the strain is removed, the elastic member 224 may contract back toward its original, relaxed length. This contraction re-establishes the corrugations of the corrugated stretch laminate 270.

In other embodiments of the present invention, the printed carrier web may be stretched in both the machine and cross-machine direction. The stretch composite preform may likewise be elongated in both the machine and cross-machine direction. The corrugated stretch laminate that results may exhibit biaxial stretch and recovery, which is the ability to stretch and recover in two orthogonal directions (e.g., machine direction and cross-machine direction). Such combination of machine direction elongation force and cross-machine direction elongation force may yield an effective force vector sum. In some instances, the force vector sum may be in a direction other than the machine direction or cross-machine direction.

In another suitable method, the carrier web may be stretched prior to application of the elastomeric composition. Stretching of the carrier web to prior to application of the elastomeric composition may performed via necking as described in U.S. Pat. Nos. 5,226,992 and 5,910,224 or via consolidation as described in U.S. Pat. Nos. 5,914,084 and 6,114,263. Necking involves the carrier web being subjected to a tensioning force in a first direction which results in the drawing or shortening of the web is a direction perpendicular to the first direction. For example, necking may involve a carrier web being tensioned in a machine direction by an apparatus such as off-speed rolls; the web is necked or drawn (e.g., shortens) in the cross machine direction. Application of an elastomeric composition may be performed while the carrier web is still in the necked state. The resulting carrier web with the elastomeric composition thereon may exhibit elasticity in a direction parallel to the necking (e.g., cross-machine direction). The carrier web with the elastomeric composition thereon can be incrementally stretched (e.g., ring-rolled) to further enhance the stretch properties.

Consolidation is another method of subjecting a carrier web, such as a neckable nonwoven, to incremental stretching in a first direction (e.g., cross-machine direction). A tensioning force is applied to the stretched carrier web in a second direction (e.g., machine direction) substantially perpendicular to the first direction to result in a stabilized, extensible, necked carrier. Application of an elastomeric composition may be performed while the carrier web is in the stabilized, extensible, necked state. The resulting carrier web with the elastomeric composition thereon may exhibit elasticity in a direction parallel to the necking (e.g., cross-machine direction). As with necking, this carrier web with the elastomeric composition thereon optionally may be incrementally stretched to further enhance stretch properties.

A variety of elastomeric compositions may be suitable for use in the present invention. Such suitable elastomeric compositions include thermoplastic elastomers that may be in the form of homopolymers (e.g., poly(isoprene)), block copolymers, random copolymers, alternating copolymers, and graft copolymers. The elastomeric composition may comprise from about 20% to about 100%, by weight, of the thermoplastic elastomer. Suitable thermoplastic elastomers may be selected from the group comprising polyvinylarenes, metallocene-catalyzed polyolefins, polyesters, polyurethanes, polyether amides, and combinations thereof. Suitable elastomeric compositons include vinylarene block copolymers. Block copolymers include variants such as diblock, triblock, tetrablock, or other multi-block copolymers having at least one vinylarene block. Exemplary vinylarene block copolymers include styrene-butadiene-styrene, styrene-isoprene-styrene, styrene-ethylenelbutylene-styrene, styrene-ethylene/propylene-styrene, and the like. Commercially available styrenic block copolymers include KRATON® from the Shell Chemical Company of Houston, Tex.; SEPTON® from Kuraray America, Inc. of New York, N.Y.; and VECTOR® from Dexco Chemical Company of Houston, Tex. Commercially available metallocene-catalyzed polyolefins include EXXPOL® and EXACT® from Exxon Chemical Company of Baytown, Tex.; AFFINITY® and ENGAGE® from Dow Chemical Company of Midland, Mich. Commercially available polyurethanes include ESTANE® from Noveon, Inc., Cleveland, Ohio. Commercial available polyether amides include PEBAX® from Atofina Chemicals of Philadelphia, Pa. Commercially available polyesters include HYTREL® from E. I. DuPont de Nemours Co., of Wilmington, Del.

The elastomeric compositions may further comprise processing aids and/or processing oils. Such aids and/or oils may be used to adjust the melt viscosity of the compositions. They include conventional processing oils, such as mineral oil, as well as other petroleum-derived oils and waxes, such as paraffinic oil, naphthenic oil, petrolatum, microcrystalline wax, paraffin or isoparaffin wax. Synthetic waxes, such as Fischer-Tropsch wax; natural waxes, such as spermaceti, carnauba, ozokerite, beeswax, candelilla, ceresin, esparto, ouricuri, rezowax, and other known mined and mineral waxes, are also suitable for use herein. Olefinic or diene oligomers and low molecular weight resins may also be used herein. The oligomers may be polypropylenes, polybutylenes, hydrogenated isoprenes, hydrogenated butadienes, or the like, with a weight average molecular weight between about 350 and about 8000.

In one embodiment, a phase change solvent may be used as the processing aid. It can be incorporated into the elastomeric composition to lower the melt viscosity, rendering the composition processable at a temperature of 175° C. or lower, without substantially compromising the elastic and mechanical properties of the composition. Typically, the phase change solvent exhibits a phase change at temperatures ranging from about 40° C. to about 250° C. The phase change solvent has the general formula:

  (I)

  (II)

  (III)

  (IV)

  (V)

a mixture thereof;

wherein Q may be a substituted or unsubstituted difunctional aromatic moiety; L is $CH_2$; R and R' are the same or different and are independently selected from H, CH3, COOH, $CONHR_1$, $CONR_1R_2$, $NHR_3$, $NR_3R_4$, hydroxy, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 1 to 7. Detailed disclosure of the phase change solvents can be found in U.S. Ser. application No. 10/429,432, filed on Jul. 2, 2003.

In addition the elastomeric composition can comprise stabilizers and the like. For example, stabilizers can include both antioxidants and light stabilizers. Suitable antioxidants include sterically hindered phenolics. A commercially available antioxidant suitable for use in the elastomeric compositions of the present invention is IRGANOX 1010 available from Ciba Specialty Chemicals North America of Tarrytown, N.Y. Suitable light stabilizers include hindered amine light stabilizers. A commercially available ultraviolet light stabilizer is TINUVIN 123 also available from Ciba Specialty Chemicals North America.

In certain embodiments, the elastomeric composition may also comprise a modifying resin. Modifying resins are particularly useful in elastomeric compositions where the thermoplastic elastomer is a block copolymer. Suitable modifying resins should associate or phase mix with soft blocks of the thermoplastic elastomer. Modifying resins should have a sufficiently high average molecular weight. Suitable modifying resins include low molecular weight elastomers and/or elastomeric precursors of the above thermoplastic elastomers, and optional crosslinkers, or combinations thereof. Modifying resins useful herein include, but are not limited to, unhydrogenated C5 hydrocarbon resins or C9 hydrocarbon resins, partially and fully hydrogenated C5 hydrocarbon resins or C9 hydrocarbon resins; cycloaliphatic resins; terpene resins; vinylarene resins; polystyrene and styrene oligomers; poly(t-butylstyrene) or oligomers thereof; rosin and rosin derivatives; coumarone indenes; polycyclopentadiene and oligomers thereof; polymethylstyrene or oligomers thereof; phenolic resins; indene polymers, oligomers and copolymers; acrylate and methacrylate oligomers, polymers, or copolymers; derivatives thereof; and combinations thereof. "C5 hydrocarbon resins" and "C9 hydrocarbon resins" are disclosed in U.S. Pat. No. 6,310,154. The elastomeric composition may comprise from about 0% to about 60%, by weight, of the modifying resin.

In one certain embodiment, the elastomeric elastomer may be formulated as described in copending U.S. patent application Ser. No. 10/610,605, filed in the name of Ashraf, et al. on Jul. 1, 2003. The elastomeric composition comprises an elastomeric block copolymer having at least one hard block and at least one soft block, a macro photoinitiator, a processing oil, and optionally, a thermoplastic polymer and/or a crosslinking agent contain such a precursor. The weight average molecular weight of the low molecular weight elastomers or elastomeric precursors is between about 45,000 and about 150,000.

Suitable elastomeric compositions for use in the processes disclosed above may exhibit a wide range of melt viscosities as determined by the Melt Viscosity Test. As shown in the examples provided below, melt viscosities less than about 100 Pa·s and in excess of about 10,000 Pa·s are clearly feasible. One skilled in the art would recognize that elastomeric compositions of viscosity between about 100 Pa·s and about 10,000 Pa·s are equally attainable for use in the processes of the present invention. As a result, it should be understood that every viscosity and range of viscosities is included as if such viscosity or range of viscosities was expressly written herein.

Suitable elastomeric compositions for use herein form elastomeric members that are elastic without further treatment. Generally, these elastomeric compositions do not include any volatile solvents with boiling point below 150° C. After the elastomeric composition has been applied to the substrate, however, post-treatments may be used to improve or enhance the elasticity and other properties including strength, modulus, and the like of the resulting elastomeric members. Typically, post-treatments converting the elastomeric compositions into elastomeric members by methods such as cooling; heating; crosslinking; curing via chemical, thermal, radiation means; ring-rolling; pressing between nip rolls, and combinations thereof.

EXAMPLES

A suitable elastomeric composition may be prepared by blending varying amounts of a styrenic elastomeric copolymer such as Vector® 4211, a sytyrene-isoprene-styrene block copolymer (SIS) from Dexco Company, Houston, Tex.; Low Molecular Weight SIS (LMW S-I-S) from Dexco Company, Houston, Tex.; Septon® 4033, a styrene-ethylene-ethylene/propylene-styrene block copolymer (SEEPS), from Septon Company of America, Pasadena, Tex.; a vinylarene resin such as polystyrene PS3900 from Nova Chemical, Inc. Moon Township, Pa.; a macro photoinitiator from National Starch and Chemicals, Bridgewater, N.J.; and mineral oil such as Drakeol® available from Penreco, Houston, Tex.

The appropriate amount of each component by weight percent of the elastomeric composition is added into a twin-screw extruder for both compounding and printing. In another approach, the elastomeric composition is pre-compounded to form a single pellet material. GLS Corporation of McHenry, Ill. is a suitable compounder for this operation. The single pellet material can be extruded for printing.

Examples of an elastomeric composition suitable for use herein are shown in Table 1. The approximate amount of each component is expressed as weight percent of the total elastomeric composition. Additives, including, for example, antioxidants and opacifiers, which are present only in small amounts, are not shown in the formulations presented in Table 1. Typically, the elastomeric compositions useful in the present invention comprise about 0.5 wt % of antioxidants, about 0.3 wt % of light stabilizers and about 3.0 wt % titanium dioxide.

TABLE 1

Elastomeric Compositions (Weight Percent)

| | Example 1 | Example 2 | Example 3 |
|---|---|---|---|
| S-I-S | 0 | 70 | 35 |
| LMW S-I-S | 0 | 0 | 20 |
| SEEPS | 55 | 0 | 0 |
| Polystyrene PS3900 | 15 | 5 | 0 |
| Mineral Oil | 30 | 25 | 40 |
| Macro-photoinitiator | 0 | 0 | 5 |

Test Method

Melt Viscosity Test

A 152 mm×152 mm aluminum mold plate containing a circular inset of 25 mm in diameter and 1.5 mm in thickness is used to prepare circular disks for the melt viscosity test. Approximately 3.0 grams of elastomeric composition (e.g., Example 1, 2, or 3) is placed in the 25 mm inset which is sitting on a sheet of Teflon. Another sheet of Teflon is placed on top of the sample/aluminum plate. A press containing heating plates, such as the Hydraulic Unit Model # 3925 available from Carver, Inc., Wabash, Ind. or another similar press, is pre-heated to a desired temperature sufficient to melt the elastomeric composition or to induce flow of the elastomeric composition. Generally, temperatures ranging from 150° C. up to 275° C. are sufficient. The mold along with Teflon sheets are placed in the Carver press for approximately one minute before closing the Carver press and applying a pressure of approximately 10,000 psi for approximately 20 seconds. The pressure is released and the sample disk is removed from the mold. The sample disk is inspected (e.g., inspection with the unaided eye, excepting standard corrective lenses, in standard lighting conditions) for defects such as, for example, air bubbles. Samples with defects present may not be tested; however, the sample may be re-heated and re-pressed to remove the defect.

The melt viscosity of elastomeric compositions can be measured using an AR1000N Rheometer available from TA Instruments, New Castle, Del. or similar rheometer. The AR1000N may be equipped an Environmental Temperature Chamber (ETC), 25mm hard anodized (HA) aluminum parallel plates, and a nitrogen purge. The rheometer may be interfaced with a computer loaded with software that controls the test conditions, records experimental data, and performs necessary analysis. A suitable computer for interface with the rheometer is the Dell Optiplex GX260 Pentium 4 Computer equipped with the Microsoft Windows XP Professional operating system. A suitable software includes Rheology Advantage Instrument Control AR, product version 4.0.1, file version 4.0.17 and Rheology Advantage Data Analysis, product version 4.0.23, file version 4.0.23; both available from TA Instruments. Calibration, sample handling and operation of the instrument may be conducted by following the manufacturer's operating procedure which are provided in an electronic format for the specific product version and file version as noted above. Modifications to the manufacturer's operating procedure are as disclosed herein.

Figure 8:
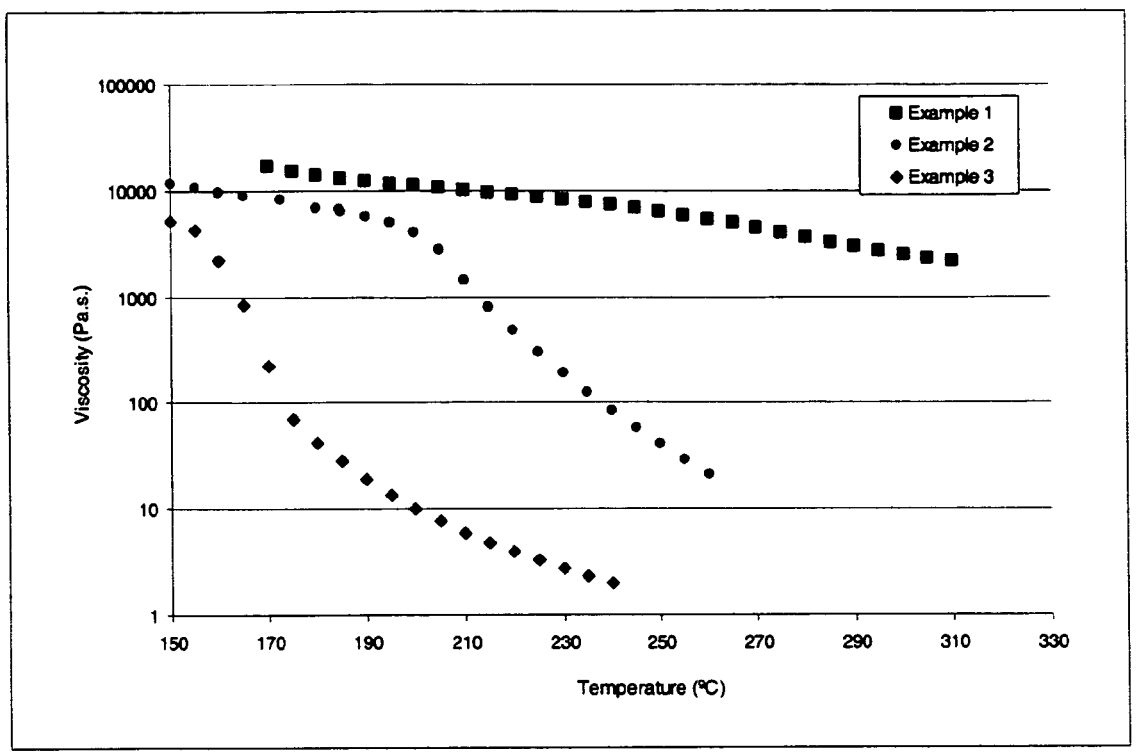
FIG. 8 is a graph plotting viscosity as a function of temperature for three formulations of the elastomeric composition.

The sample is placed between the rheometer's two 25 mm diameter parallel plates with an initial gap of 1.5 mm between the plates. The sample chamber is heated to 150° C. until it is equilibrated and the sample reaches 150° C. The gap is reduced to 1.0 mm. The melt viscosity is measured under temperature sweep test as described below:

Start Temperature: 150° C.
Final Temperature: 300° C.
Temperature Increment: 5° C.
Strain: 5%
Frequency: 1 radians/sec
Log Mode
Gap - 1000 μm During the sweep, temperature changes and data collection are done incrementally. The sample chamber is heated to the prescribed temperature (e.g., 150° C., 155° C., 160° C., and so forth to 300° C.). Once the sample reaches the prescribed temperature, a one minute delay occurs and then data is collected. The sample chamber is heated to raise the sample chamber temperature by an increment of 5° C. and the process is repeated. The resulting data for Examples 1, 2, and 3 are shown in the graph of FIG. 8 as function of viscosity (Pa·s) versus temperature (° C.).

Suitable uses for the corrugated stretch laminates that result from the processes of the present invention include use within disposable articles. Exemplary disposable articles include diapers, training pants, adult incontinence articles, sanitary napkins, garments like gloves, aprons, smocks, socks, etc. Exemplary disposable article construction is described generally in U.S. Pat. Nos. 3,848,594; 3,860,003; 4,662,875; 4,846,815; 4,894,060; 4,946,527; 5,151,092; 5,221,274; 5,554,145; 5,569,234; 5,580,411; 6,004,306; and 6,432,098 and in U.S. application Ser. No. 10/764,850. The disposable articles described in these patents and applications may comprise a variety of elements that require elastic regions. Such elements include, for example, ears, leg cuffs, waist bands, back panels, front panels, side panels, topsheets, fastener systems (e.g., tape tabs, hook and loop fastening components, interlocking fasteners such as tabs & slots, buckles, buttons, snaps, and/or hermaphroditic fastening components, and any other known fastening means), and combinations thereof. Elastic regions may comprise the corrugated stretch laminates that are manufactured via the process of the present invention. Furthermore, U.S. application No. 60/557,288 describes an absorbent article that comprises at least one stretch zone wherein the stretch zone comprises an elastomeric composition. The corrugated stretch laminate resulting from the processes of the present invention may be used to provide such stretch zones.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a corrugated stretch laminate comprising the steps of:
   a) providing a first carrier web having a first surface and a second surface;
   b) applying a first elastomeric composition in a fluid or molten state to the first surface of the carrier web to form at least one first elastic member, wherein the first elastomeric composition exhibits a melt viscosity of greater than about 10,000 Pa·s at 175° C.;
   c) incrementally stretching in a first direction at least a portion of the carrier web to form a stretch composite preform;
   d) elongating the stretch composite preform in the first direction;
   e) joining a first substrate to the elongated stretch composite preform; and
   f) allowing the elongated stretch composite preform to recover to form said corrugated stretch laminate.

2. The process of claim 1 wherein the step of applying the first elastomeric composition is performed directly or indirectly.

3. The process of claim 1 wherein the step of applying the first elastomeric composition is performed by applying the first elastomeric composition with a device selected from the group consisting of baths, slot coaters, sprayers, porous rolls, extruders, print rolls, print webs, gravure rolls, gravure webs, reverse rolls, knife-over rolls, notched knife-over rolls, metering rods, curtain coaters, air knife coaters, and combinations thereof.

4. The process of claim 1 further comprising the step of applying a second elastomeric composition in a fluid or molten state to the carrier web to form at least one second elastic member.

5. The process of claim 4 wherein said first elastic member and said second elastic member differ in a property selected from the group consisting of elasticity, melt viscosity, shape, pattern, add-on level, formulation, and combinations thereof.

6. The process of claim 1 further comprising the step of treating said first elastomeric composition, wherein said treating is selected from the group consisting of crosslinking, curing, drying, cooling, ring-rolling, heating, and combinations thereof.

7. The process of claim 1 wherein the first elastic composition is selected from the group consisting of styrenic block copolymers, polyolefins, polyesters, polyurethanes, polyether amides, and combinations thereof.

8. The process of claim 1 wherein the incremental stretching of the carrier web is performed by ring-rolling.

9. The process of claim 1 wherein the elongation of the carrier web is performed by a device selected from the group consisting of Mount Hope rolls, off-speed rolls, tentering frames, angled idlers, angled nips, slatted spread rollers, edge pull web stretchers, and combinations thereof.

10. The process of claim 1 further comprising the step of joining a second substrate to the carrier web and/or the stretch composite preform.

11. The process of claim 1 wherein the corrugated stretch laminate comprises at least one corrugation.

12. The process of claim 1 wherein said elastomeric composition comprises:
   a) from about 20 to about 100 weight percent of a thermoplastic elastomer which is a block copolymer having at least one hard block comprising vinylarenes and at least one soft block comprising dienes;
   b) from about 0 to about 60 weight percent of a processing oil; and
   c) from about 0 to about 60 weight percent of at least one vinylarene resin.

13. The process of claim 1 further comprising a step of joining the corrugated stretch laminate into an absorbent article.

14. The process of claim 13 wherein said corrugated stretch laminate is provided in an element of the absorbent article selected from the group consisting of a waist feature, a cuff, a side panel, an ear, a backsheet, a topsheet, a fastener system, and combinations thereof.

15. The process of claim 1 wherein the first direction is a machine direction.

16. The process of claim 1 wherein the first direction is a cross-machine direction.

* * * * *

UNITED STATES PATENT AND TRADEMARK OFFICE
CERTIFICATE OF CORRECTION

PATENT NO. : 7,501,034 B2
APPLICATION NO. : 10/966759
DATED : March 10, 2009
INVENTOR(S) : Arman Ashraf It is certified that error appears in the above-identified patent and that said Letters Patent is hereby corrected as shown below:

Column 16
Line 59, delete "styrene-ethylenelbutylene-styrene," and insert
-- styrene-ethylene/butylene-styrene, --.

Signed and Sealed this

Tenth Day of November, 2009

David J. Kappos
*Director of the United States Patent and Trademark Office*